United States Patent
Barazani

(10) Patent No.: US 8,142,804 B2
(45) Date of Patent: Mar. 27, 2012

(54) PEST CONTROL SHEET

(75) Inventor: Avner Barazani, Omer (IL)

(73) Assignee: Makhteshim Chemical Works Ltd., Beer Sheva (IL)

( * ) Notice: Subject to any disclaimer, the term of this patent is extended or adjusted under 35 U.S.C. 154(b) by 138 days.

(21) Appl. No.: 12/129,411

(22) Filed: May 29, 2008

(65) Prior Publication Data

US 2008/0312086 A1    Dec. 18, 2008

Related U.S. Application Data

(62) Division of application No. 10/415,550, filed as application No. PCT/IL01/01014 on Nov. 1, 2001.

(30) Foreign Application Priority Data

Nov. 1, 2000 (IL) .......................................... 139388

(51) Int. Cl.
*A01N 25/00* (2006.01)
(52) U.S. Cl. ............ 424/411; 47/9; 47/29; 47/DIG. 11; 424/78.31; 424/78.35; 424/78.37; 424/403; 424/404; 424/406; 504/116; 504/118; 504/189; 504/209; 504/351; 428/212; 428/474.4; 428/474.7; 428/480; 428/500; 428/516; 428/518; 428/907; 514/520; 514/531; 514/532; 514/383; 514/385; 514/407; 523/122
(58) Field of Classification Search .................. 424/409, 424/411
See application file for complete search history.

(56) References Cited

U.S. PATENT DOCUMENTS

| | | | |
|---|---|---|---|
| 3,591,361 A | 7/1971 | Ishimoto | |
| 3,939,606 A | 2/1976 | Vandemark et al. | 47/9 |
| 4,160,335 A | 7/1979 | Von Kohorn et al. | |
| 4,666,767 A | 5/1987 | Von Kohorn et al. | 424/410 |
| 4,743,448 A | 5/1988 | Bahadir et al. | |
| 5,116,414 A | 5/1992 | Burton et al. | 504/347 |
| 5,139,566 A | 8/1992 | Zimmerman | |
| 5,178,495 A | 1/1993 | Cameron | 405/303 |
| 5,181,952 A | 1/1993 | Burton et al. | |
| 5,575,112 A | 11/1996 | Scheubel | |
| 5,856,271 A | 1/1999 | Cataldo et al. | |
| 5,866,269 A | 2/1999 | Dalebroux et al. | |
| 6,060,076 A | 5/2000 | Voris et al. | |

FOREIGN PATENT DOCUMENTS

| | | |
|---|---|---|
| ES | 419946 A1 | 4/1976 |
| ES | 2182365 | 8/2000 |
| ES | 2198004 A1 | 1/2004 |
| GB | 1 378 663 | 12/1974 |
| GB | 1481693 | 8/1977 |

(Continued)

OTHER PUBLICATIONS

Abstracts for: JP 2000041418, "Seed Mat with Film for Germination of Lawn", Gorin Int Co Ltd et al., Feb. 15, 2000.

(Continued)

*Primary Examiner* — Neil Levy
(74) *Attorney, Agent, or Firm* — Browdy and Neimark, PLLC

(57) ABSTRACT

A sheet for pest control, wherein said sheet is of polymeric material and comprises at least two layers; a top layer and a bottom layer, wherein the bottom layer contains a herbicide and one or more pesticides selected from among fungicides and insecticides, and the top layer optionally containing an insecticide and/or fungicide. Other aspects of the invention include a polymeric composition used in the preparation of the sheets and a method for pest control in agriculture, horticulture and gardens.

24 Claims, 3 Drawing Sheets

FOREIGN PATENT DOCUMENTS

| | | | |
|---|---|---|---|
| GB | 1481693 | A | 8/1977 |
| JP | 58032944 | B | 2/1983 |
| JP | 62-175129 | | 7/1987 |
| JP | 62175129 | | 7/1987 |
| JP | 63-175072 | | 7/1988 |
| JP | 6054603 | A2 | 3/1994 |
| JP | 6197676 | A2 | 7/1994 |
| JP | 12-041418 | | 2/2000 |
| WO | 98/07318 | A2 | 1/1998 |
| WO | WO 99/23872 | | 5/1999 |
| WO | 00/11930 | A1 | 3/2000 |
| WO | WO 00/11930 | A1 | 3/2000 |

OTHER PUBLICATIONS

Abstract for: FR 2,206,051, "Dispensers of the Controlled Release of Pest-Controlling Agents and Methods for Combatting Pests Therewith", Herculite Protective Fab, Jul. 10, 1979.

Bahadir et al Field Trials with Desmetryn containing cover and mulch sheets to control weeds in white cabbage cultivation Zeitschrift Fuer Pflanzenkrankheiten Und Pflanzeischutz 1987 94(1), p. 34,35.

JP62-175129 Partial English Translation.

FIGURE I
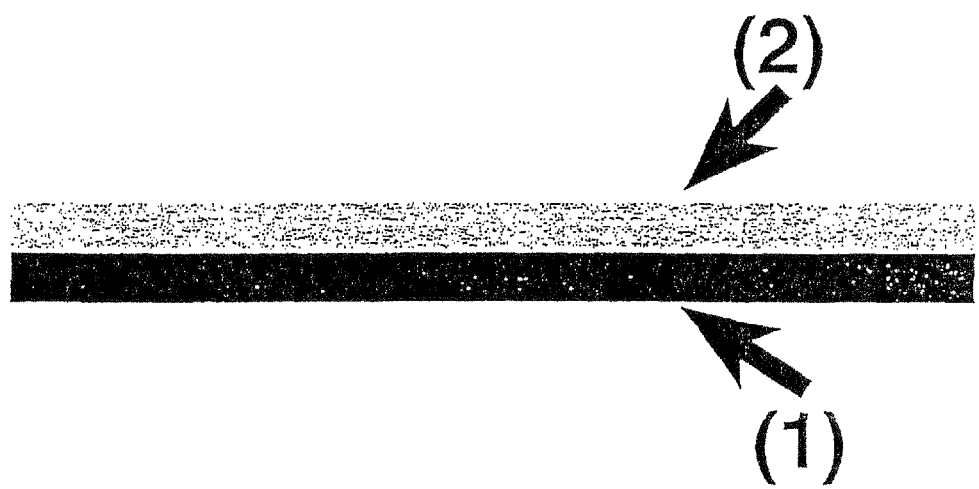

FIGURE II
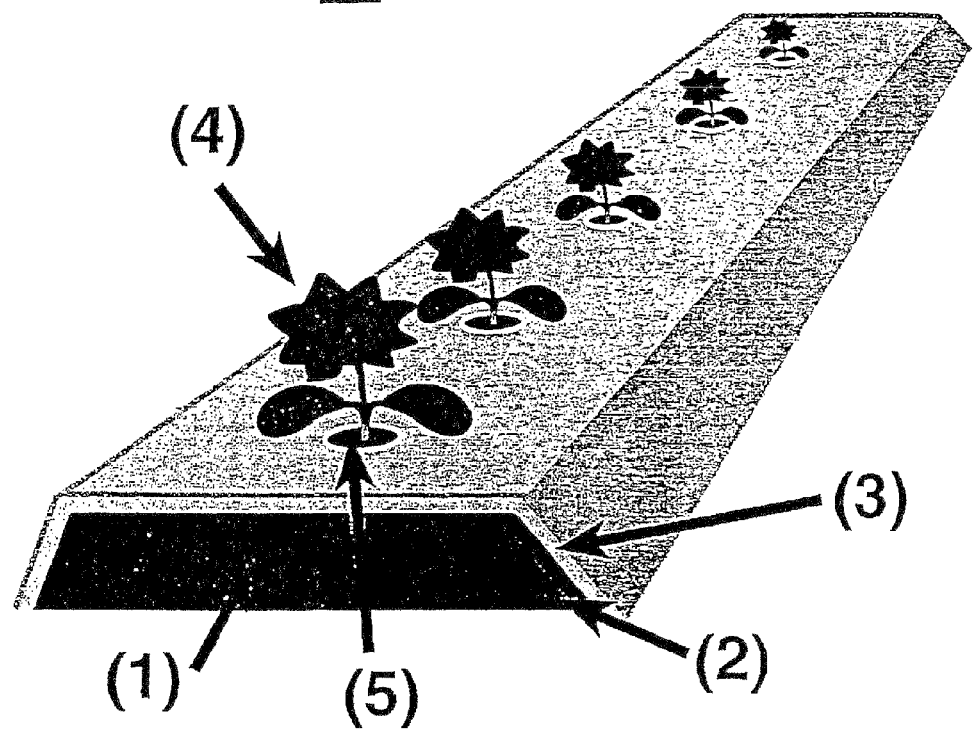
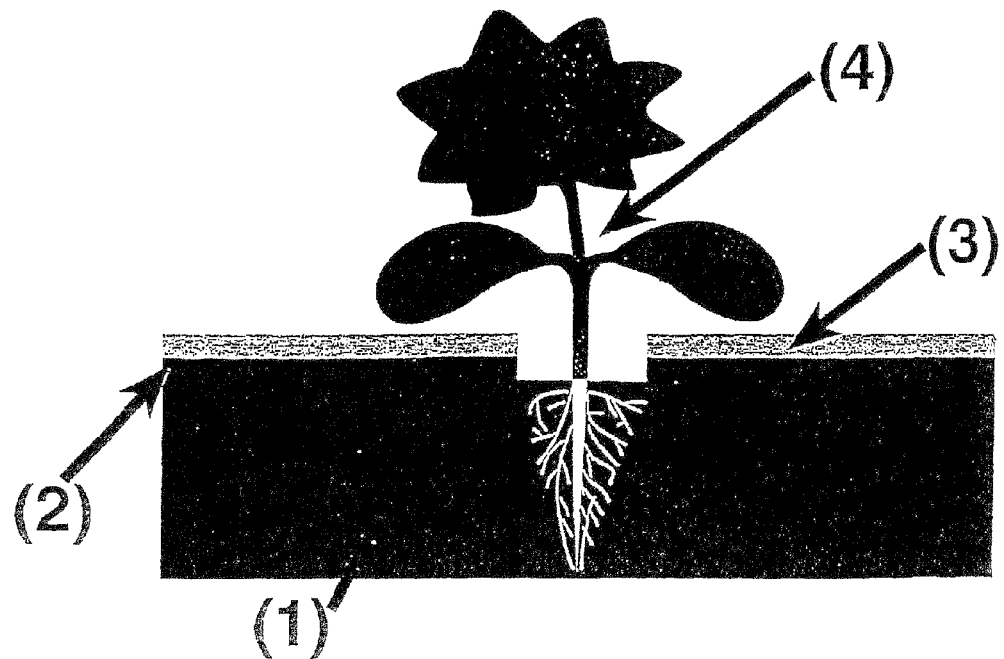

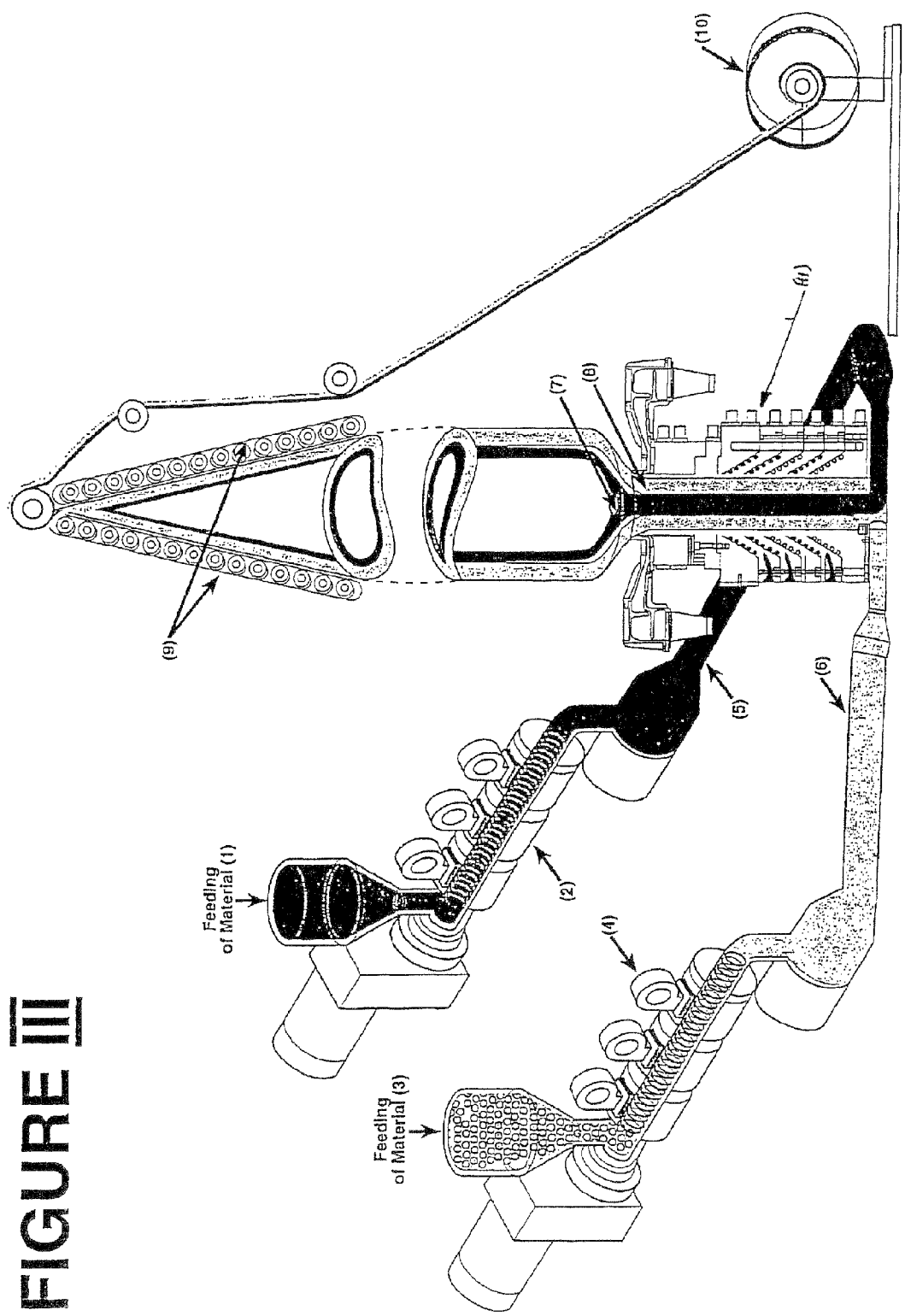

PEST CONTROL SHEET

FIELD OF THE INVENTION

The present invention relates to the field of pest control. Particularly, to a novel polymeric sheet and uses thereof in pest control in agriculture, horticulture and gardens.

BACKGROUND OF THE INVENTION

The control of pests is a vast field which covers a plethora of methods, devices and compositions. The control of weeds via sheets which contain a herbicide are known in the art. U.S. Pat. No. 5,181,952 discloses a herbicide-containing-geotextile which is used for preventing the entry of roots into soil. The geotextile can be inserted in the soil to form a barrier so that roots may not penetrate the barrier, and thus, the soil beyond the banner is protected from the intrusion of roots and subsequent damage which may result therefrom. The herbicide is distributed in various forms throughout the geotextile. U.S. Pat. No. 5,575,112 discloses a similar fabric to that of U.S. Pat. No. 5,181,952 and use thereof for controlling root growth. Said fabric comprises an inorganic copper compound as a herbicide. U.S. Pat. No. 5,139,566 to Reemay Inc. describes a geotextile and use thereof, similar to the above-referenced publications. The sheets described in the prior art cannot be applied in agriculture as weed control sheets for protecting a field of crop. The manner in which the herbicide is dispersed throughout the sheets which are described in the prior art, is not suitable for said agricultural application. Applying said sheets would expose the crop to the herbicide which would result in damage to the crop and subsequent withering of the plant.

Other methods of pest control in agricultural fields include pretreatment of the soil with methyl bromide. Methyl bromide is a highly effective and controversial pest controlling agent. It is alleged to have hazardous impact on the environment, and thus will most likely be ban for use in the future.

Furthermore, there are certain crops which are highly sensitive to herbicides. For example cucurbitaceae (zucchini, cucumbers, melons, watermelons squash and the like) are very sensitive to herbicides. Thus, the only way for removing weeds from the a field of cucurbitaceae is by manual means.

In view of the aforementioned there is a long felt need to develop a method and means for pest control which provides a solution to the aforementioned disadvantages. Further more there is a long felt need to develop a pesticide control sheet which can be effectively and safely applied for agricultural purposes.

It is therefore an objective of the present invention to provide a pesticide control sheet which can be-used in agriculture.

It is another objective of the present invention to provide a method for pest control in agriculture which provides highly effective pest control and is safe to the plant and crop.

A further objective of the present invention is to provide a composition for preparing a pest control sheet.

It is yet another objective of the present invention to provide a sheet and method for pest control that overcome the disadvantages of the known art.

Other objectives of the invention will become apparent as the description proceeds.

The term sheet is synonymous with film.

SUMMARY OF THE INVENTION

The present invention provides a sheet for pest control, wherein said sheet is of polymeric material and comprises at least two layers; a top layer and a bottom layer. The bottom layer contains a herbicide and optionally a pesticide selected from among insecticides and fungicides. The top layer is a protective layer to protect the plant parts, which can be harmed by the pesticide in the bottom layer, from coming in contact with the bottom layer. Optionally, the top layer may contain an insecticide to protect the plant from insect infestation and a fungicide to protect the plant from fungus attack. Said sheet may further optionally comprise an additional layer or layers which function as a barrier between the bottom layer and the top layer, hereinafter protective middle layer.

Further provided by the present invention is a method for pest control in agriculture, horticulture and gardening, comprising covering the ground (soil) with the sheet of the present invention. Hence, the bottom layer prevents the emergence of weeds and controls soil borne pests. The top layer protects the sensitive plant parts from contacting the bottom layer. When the top layer contains an insecticide and/or fungicide, said layer further protects the plant from insect infestation.

Furthermore, the present invention provides compositions comprising a polymer and a pesticide, hereinafter "master batch", which are suitable for the preparation of polymeric sheets, and wherein the layers of the sheet of the present invention are produced from said master batch. The master batch may be in the form of a resin, wherein the pesticide is mixed into the resin, or in the form of pellets which contain the pesticide.

Throughout the description of the invention the term "pesticide" applies to herbicides, fungicides and insecticides.

DESCRIPTION OF THE DRAWINGS

FIG. I is a cross section of a particular embodiment of the sheet.

FIG. II is a cross section of a crop field in which the. method of the present invention has been applied.

FIG. III is a schematic representation of a process for preparing the sheet.

DETAILED DESCRIPTION OF A PREFERRED EMBODIMENT OF THE INVENTION

The following description is illustrative of embodiments of the invention, with reference to the Figures. The following description is not to be construed as limiting, it being understood that the skilled person may carry out many obvious variations to the invention.

Throughout the description, percentage indicated are by weight.

According to an embodiment of the present invention the sheet of the present invention is of polymeric material which is suitable for use as a ground sheet. Said polymeric material selected from a group comprising homopolymers and copolymers of polyolefines selected from a group comprising of low density polyethylene (LDPE), high density polyethylene (HDPE), polypropylene (PP), ethylene vinyl acetate (EVA), ethylene methyl acrylate (EMA), derivatives or mixtures and blends thereof. Other polymeric materials can be used for the present invention, as may be appreciated by the skilled artisan. The sheet is composed of at least two layers of polymeric material wherein the bottom layer [FIG. I, (1)] contains about 0.1% to 5% herbicide, and optionally 0.1% to 5% of one or more other pesticides, and the top layer [FIG. I, (2)] is a polymer layer which protects parts of the plants such as leaves and the shoot from contacting the bottom layer. Contact of the leaves or the shoot with the herbicide in the bottom layer would result in damage to the plant which subsequently could result in withering of the plant. The top layer may optionally contain a fungicide or insecticide, Control of weeds is provided in two manners; 1) weeds emerging from the ground contact the bottom layer and the herbicide in this layer and are thus eliminated 2) The herbicide is slowly released from the bottom layer and migrates into the soil, hence preventing the emergence of weeds from the soil.

The rate of release of the pesticide from the sheet is controlled so that by the end of the growing season most, and may be all, of the pesticide has been released from the sheet. The rate of release of the pesticide from the sheet may be controlled by the amount and type of anti-block. filler additives and type of polymer from which the sheet is prepared. Said additives described hereinafter.

According to a further embodiment of the invention the bottom layer contains about 0.1% to 5% herbicide and about 0.1% to 5% insecticide and/or fungicide. Thus, the bottom layer controls weeds and exterminates soil dwelling insects which could be harmful for the plant, and protects and controls fungus attack. According to the present embodiment insect control is achieved by an insecticide which migrates from the bottom layer into the soil and/or via contact of the insect with the insecticide-containing bottom layer.

In accordance to yet a further embodiment of the invention the top layer contains about 0.1% to 5% insecticide and/or fungicide. Hence, providing control of insects and disease around the parts of the plant which are above the sheet. Insects coming in contact with the insecticide in the top layer will accordingly be exterminated and the fungicide provides protection against fungi.

According to a further embodiment, the sheet of the present invention may further comprise an additional layer or layers of polymeric film between the top and bottom layer. Said protective middle layer being of a polymeric material which prevents the migration of herbicide from the bottom layer to the top layer and subsequently to the plant. Thus any migration of the herbicide or vapor thereof upwards is prevented, hence a "sealing" effect is obtained. The protective middle layer may be a polyamide, polyvinyly alcohol or any other polymeric material which provides said sealing effect.

Herbicides suitable for use in the present invention are selected from a group comprising, but not limited to: Oxyfluorfen-2-chloro-a,a,a-trifluoro-p-tolyl 3-ethoxy-4-nitrophenyl ether Trifluralin-a,a,a-trifluoro-2,6-dinitro-N,N-dipropyl-p-toluidine Benfluralin-N-butyl-N-ethyl-2,6-dinitro-4 (trifluoromethyl)benzenamine Isopropalin-4-isopropyl-2,6-dinitro-N,N-dipropylaniline Oryzalin-3,5-dinitro-N4,N4-dipropylsulfanilamide Fluoroxypyr-4-amino-3,5-dichloro-6-ELuoro-2-pyridyloxyacetic acid Ethalfluralin-N-ethyl-a,a,a-trifluoro-N-(methylallyl)-2,6-dinitro-p-toluidine Pendimethalin-N-(1-ethylpropyl)-2,6-dinitro-3,4-xylidine Profluralin-N-(cyclopropylmethyl)-a,a, a-trifluoro-2,6-dinitro-N-propyl-p-toluidine Diuron-3-(3,4-dichlorophenyl)-N,N-dimethylurea Imazethapyr-(RS)-5-ethyl-2-(4-isopropyl-4-methyl-5-oxo-2-imidazolin-2-yl) nicotinic acid Imazaquin-(RS)-2-(4-isopropyl-4-methyl-5-oxo-2-imidazolin-2-yl) quinoline-3-carboxylic acid Glyphosate-N-(phosphonomethyl)glycine Simazine-6-chloro-N,N'-diethyl-1,3,5-triazine-2,4-diamine Terbutryn-N-(1,1-dimethylethyl)-N'-ethyl-6-(methylthio)-1,3,5-triazine-2,4-diamine Metribuzin-4-amino-6-tert-butyl-3-methylthio-1,2,4-triazin-5 (4H)-one or sulfonyl urea herbicides selected from among (common names) triasulfuron, clorsulfuron, tribenuron and rimsulfuron.

Insecticides useful for the present invention (noted according to the common names) are selected from among the following groups of insecticides comprising, but not limited to, the following insecticides: organophosphorous insecticides: chlorpyrifos and diazinon; neonicotinoids: imidacloprid, acetamiprid, thiamethoxam; pyrethroid inseticdes: bifenthrin, lambda-cyhalothrin, tefluthrin and permathrin. Further suitable insecticides are spinosad, indoxacarb, fipronil and insecticides of the group known as nematicides, such as cadusafos and fenamiphos.

Fungicides useful for the present invention (noted according to the common names) are selected from among, but not limited to, a group of fungicides which are steroid demethylation inhibitors (SDI). The group of SDI comprises hexaconazole, myclobutanil, propiconazole, triadimenol, tebuconazole, penconazole. Other useful fungicides are prochloraz, metalaxyl, dimethomorph, cymoxanil, propamocarb hydrochloride and fluazinam. Further fungicides useful for the present invention are of the group known as strobilurin type fungicides, such as: Azoxystrobin, Kresoxim-methyl, Trifloxystrobin, Metonimostrobin, Picoxystrobin, Pyraclostrobin, MA-20565 (development code of Mitsubishi) According to a preferred embodiment, the sheet of the present invention is transparent.

This allows for the heating of the soil via the "green house effect". This effect occurs when solar radiation penetrates the sheet and is reflected from the soil. The reflected radiation in the infra-red range does not penetrate the sheet and is thus "trapped" between the sheet and the soil. This "trapped" radiation heats the soil. This is particularly important in cold countries of for crops that are grown during cold seasons.

The present invention further provides a method for pest control. Said method may be applied in agriculture, horticulture or in garden maintenance. In agriculture and horticulture said method is applied as follows: subsequent to physically preparing the field and soil for planting, e.g. plowing, fumigating the soil and laying down of an irrigation system, the sheet is spread over the field so as to cover the soil [FIG. II, (1)], and is then secured to the ground. The sheet [FIG. II, (2), (3)] is then punctured at the spot where a seedling is intended to be planted so that a seedling [FIG. II, (4)] may be inserted through the hole [FIG. II, (5)] and planted in the soil. The seedling is planted in such a manner that the roots are in the soil and the leaves are above the top layer in a manner that they do not come in contact with the bottom layer. Thus, the herbicide, and optionally the insecticide in the bottom layer, control weeds, and optionally insects, via contact of the weed or insect with the bottom layer or via slow release of the pesticides into the soil, hence controlling the emergence of weeds and exterminating insects in the soil. When the sheet contains a pesticide in the top layer, then pest control is maintained above the soil, in the area of the plant. This may also help in protecting the fruit/vegetable itself. Said method can be applied in gardens in a similar manner as described above.

The method of the present invention presents the following advantages:

1. The application of the sheet to the field is done before the plants are planted and is a single step application. Thus, there is no need to remove the sheet until after harvest time.
2. The sheet provides constant pest control throughout the entire growing season, without the need to reapply pesticides during the season.
3. The method provides a safe mode of pesticide application. The pesticides are released slowly directly into the ground or affixed to the sheet. Hence the exposure of people working in the field is minimal. This is in comparison to other application methods which involve handling and mixing of toxic chemicals and spraying of these chemicals. The spraying creates a hazardous mist which may be harmful to the person working in the field and to the environment 4. The pesticide release profile of the sheet is such that by the end of the season when the sheet may be collected from the field there is none, or minimal traces of pesticide in the sheet, which allows for the recycling of the polymeric sheet.

This has its environmental advantages.

5. For crops which are sensitive to herbicides, the present invention provides an effective substitute for methyl bromide which is allegedly harmful to the environment and is often used for such crops.
6. The sheet further provides a green house effect.

In yet a further embodiment of the present invention the master batch comprises about 5% to 30% by weight pesticide, wherein the herbicide content in the master batch intended for the preparation of the bottom layer, contains about 5% to 30% herbicide and optionally 5% to 30% of insecticide and 5% to 30% of fungicide. According to an optional embodiment wherein the top layer comprises a fungicide and/or an insecticide, a master batch intended for the preparation of the top layer comprises 5% to 30% of insecticide. Hereinafter a master batch without a pesticide is defined as "pre-mix".

According to a particular embodiment of the invention the master batch is in the form polymeric pellets which contain a pesticide. According to a preferred embodiment of the invention, the master batch for preparing the bottom layer (hereinafter "bottom master batch") comprises polyethylene pellets containing about 5% to 30% oxyfluorfen in the pellet. In yet a further embodiment, the bottom master batch comprises about 5% to 30% oxyfluorfen and about 5% to 30% insecticide selected from among diazinon, chlorpyrifos and imidacloprid. The master batch for preparing the top layer, according to the embodiment wherein the top layer comprises an insecticide, is defined as the top master batch and comprises about 5% to 30% insecticide selected from among diazinon, chlorpyrifos and imidacloprid. The top master batch may be in the form polymeric pellets wherein the insecticide is dispersed throughout the pellet.

The master batch may be prepared during the manufacturing process of the sheet by directly adding the required amount of pesticide to the pre-mix in the polymer-sheet-preparing-apparatus which may be an extruder or any other polymer-sheet-manufacturing apparatus.

The sheet of the present invention may further be prepared by applying to a ready polymeric sheet which comprises a bottom and top layer, a pesticide. Thus, obtaining a sheet as described herein.

The pre-mix and master batches of the present invention may further comprise additives that are intended for achieving the desired properties of the sheet. The group of additives which are well known from the prior art comprises u. v. absorbents; anti-blocks which are based on amorphous and crystalline silicates; slip agents selected from among amides, oleamide, stearamide and derivatives thereof; lubricants selected from among polyolefine waxes, PE waxes and PP waxes and metal stearates; anti-oxidants. Other additives may be applied as may be appreciated by the skilled artisan.

Throughout the description, where herbicide, insecticide or fungicide is described in the invention, it also includes mixtures thereof.

The following description is for purposes of illustration and is not to be construed as limiting. The sheet of the present invention can be produced from a pre-mix or a top master batch, and a bottom master batch according to a technique known by the skilled artisan as co-extrusion blown film technique. According to said technique, the bottom master batch and polymeric resin are fed to an extruder [FIG. III, the are extruded under heat [FIG. III, (2), (5)], while simultaneously, the top master batch or top pre-mix is fed to a separate extruder together with polymeric resin [FIG. II, (3)] and extruded under heat [FIG. III, (4), (6)]. The final desired percentage of pesticide in each layer can be adjusted by controlling the amount of polymeric resin added to each mixture. Both extruded mixtures are fed to the blowing tower [FIG. III, (11)] wherein they are simultaneously blown into two films each blown through a separate die. The top master batch or pre-mix is blown to form a balloon, hereinafter "outer balloon", while simultaneously, the bottom master batch is also blown to from a balloon which is contained within the outer balloon. The dies through which the balloons are blown are arranged such that the inner die is set in the center of the outer die. The bottom layer of the sheet is formed through the inner die [FIG. III, (7)] and the top layer of the sheet is formed through the outer die [FIG. III, (8)]. The films which form the balloon-within-a-balloon formation are pressed and flattened between rollers [FIG. III, (9)] and rolled as a four layered sheet [FIG. III, (10)]. The four layer pressed sheet is then cut and spread open to form the bi-layer sheet of the present invention. By cutting and spreading the four layer sheet, the inner two layers of the four layer sheet for the bottom layer of the sheet of the present invention, and the outer two layers of the four layer sheet form the top-layer of the sheet of the present invention.

The foregoing technique is also suitable for preparing a sheet with more than two layers. In such a case the co-extrusion is carried out with more than two master batches and/or pre-mix. Accordingly, a sheet with a protective middle layer may be produced by said technique.

Other polymer-sheet-forming techniques known in the art may be applied for the purpose of preparing the sheet of the present invention.

While the method of the present invention may be broadly applied in the fields of agricultural and gardening, a particularly effective application of the method is for crops selected from among: cucurbitacea: melon, Zucchini, cucumber, watermelon, squash; solanaceae: tomato, pepper, eggplants orchards and ornamentals.

EXAMPLES

Example 1

Watermelon Crop

The sheet and method of the present invention have been applied to a watermelon crop. The experiments were conducted with three different concentrations of herbicide in the bottom layer. The results are presented in Table I.

TABLE I

| Pesticide | % Pesticide* | Development¥ | Weed control§ |
|---|---|---|---|
| Oxyfluorfen | 0.5 | 100 | 100 |
| Oxyfluorfen | 1 | 100 | 100 |
| Oxyfluorfen | 2 | 100 | 100 |

*weight % of pesticide in bottom layer of sheet
¥% of crop development in comparison to healthy crop on a scale of 0-100, 100 indicating a healthy crop.
§% of weed control on a scale of 0-100, 100 indicating total prevention of weed emergence.

Example 2

Preparation of Bottom Master Batch

The following is a description of the preparation of 100 kg master batch. 2.5 kg of a composition of additives is prepared by mixing slip agents, anti-oxidants and lubricant in a weight ratio of about 2: 2: 6.67.5 kg of EVA resin, 10 kg anti-block Apace 10063 and 2.5 kg of the above additive composition are fed to the main feeding port of the extruder, thus forming a polymeric melt. Each component has a separate continuos-weight feeder. 20 kg oxyfluorfen is mixed with the polymeric melt in the center of the extruder. The final polymeric melt obtained is fed through a perforated disc to form "noodle like" polymeric strands which are slowly cooled and chopped and fed into a pelletizer/granulator.

While embodiments of the invention have been described by way of illustration, it will be apparent that the invention may be carried out with many modifications, variations and adaptations, without departing from its spirit or exceeding the scope of the claims.

What is claimed is:

1. A sheet for pest control, wherein said sheet is of polymeric material and comprises at least a top protective layer, a barrier middle layer and an herbicidal bottom layer;
   a. wherein the bottom layer contains a herbicide and optionally one or more pesticides selected from the group consisting of fungicides and insecticides;
   b. the top layer contains at least one of an insecticide and a fungicide;
   c. the barrier middle layer being adapted to protect plant parts from coming into contact with the herbicidal bottom layer.

2. The sheet according to claim 1, wherein the top layer contains an insecticide and a fungicide.

3. The sheet according to claim 1, wherein the bottom layer contains a herbicide and an insecticide and the top layer contains an insecticide.

4. The sheet according to claim 1, wherein the bottom layer contains a herbicide, a fungicide and an insecticide and the top layer contains an insecticide.

5. The sheet according to claim 1, wherein the bottom layer contains a herbicide, a fungicide and an insecticide and the top layer contains an insecticide and fungicide.

6. The sheet according to claim 1, wherein the bottom layer contains a herbicide, a fungicide and an insecticide, and the top layer contains a fungicide.

7. The sheet according to claim 1, wherein said sheet is suitable for use as a ground cover sheet.

8. The sheet according to claim 1, wherein said polymeric material is a homopolymer or copolymer of a polyolefin.

9. The sheet according to claim 8, wherein the barrier middle layer is of polyamide or polyvinyl alcohol polymer.

10. The sheet according to claim 1, wherein the bottom layer contains about 0.1% to 5% herbicide.

11. The sheet according to claim 10, wherein the bottom layer further contains about 0.1% to 5% insecticide and/or 0.1% to 5% fungicide.

12. The sheet according to claim 10, wherein the top layer contains about 0.1% to 5% insecticide and/or 0.1% to 5% fungicide.

13. The sheet according to claim 11, wherein the top layer contains about 0.1% to 5% insecticide and/or 0.1% to 5% fungicide.

14. The sheet according to claim 1, wherein the herbicide is selected from the group consisting of:
   Oxyfluorfen-2-chloro-$\alpha,\alpha,\alpha$-trifluoro-p-tolyl 3-ethoxy-4-nitrophenyl ether
   Trifluralin-$\alpha,\alpha,\alpha$-trifluoro-2,6-dinitro-N,N-dipropyl-p-toluidine
   Benfluralin-N-butyl-N-ethyl-2,6-dinitro-4-(trifluoromethyl)benzenamine
   Isopropalin-4-isopropyl-2,6-dinitro-N,N-dipropylaniline
   Oryzalin-3,5-dinitro-$N^4,N^4$-dipropylsulfanilamide
   Fluroxypyr-4-amino-3,5-dichloro-6-fluoro-2-pyridyloxy-acetic acid
   Ethalfluralin-N-ethyl-$\alpha,\alpha,\alpha$-trifluoro-N-(methylallyl)-2,6-dinitro-p-toluidine
   Pendimethalin-N-(1-ethylpropyl)-2,6-dinitro-3,4-xylidine
   Profluralin-N-(cyclopropylmethyl)-$\alpha,\alpha,\alpha$-trifluoro-2,6-dinitro-N-propyl-p-toluidine
   Diuron-3-(3,4-dichlorophenyl)-N,N-dimethylurea
   Imazethapyr-(RS)-5ethyl-2-(4-isopropyl-4-methyl-5-oxo-2-imidazolin-2-yl)nicotinic acid
   Imazaquin-(RS)-2-(4-isopropy-4-methyl-5-oxo-2-imidazolin-2-yl)quinoline-3-carboxylic acid
   Glyphosate-N-(phosphonomethyl)glycine Simazine-6-chloro-N,N'-diethyl-1,3,5-triazine-2,4-diamine
   Terbutryn-N-(1,1-dimethylethyl)-N'-ethyl-6-(methylthio)-1,3,5-triazine-2,4-diamine
   Metribuzin-4-amino-6-tert-butyl-3-methylthio-1,2,4-triazin-5(4H)-one, or sulfonyl urea herbicides selected from among triasulfuron, clorsulfuron, tribenuron and rimsulfuron.

15. The sheet according to claim 1, wherein the insecticide is selected from the group consisting of: organophosphorous insecticides; neonicotinoids; pyrethroid insecticides; nematicides; and spinosad, indoxacarb and fipronil.

16. The sheet according to claim 1, wherein the fungicide is selected from the group consisting of fungicides which are steroid demethylation inhibitors; and strobilurin type fungicides.

17. The sheet according to claim 1, wherein the sheet is transparent.

18. The sheet according to claim 1 wherein the pesticide in the bottom layer is selected from the group consisting of herbicides, insecticides, mixtures of herbicides, mixtures of insecticides, and combinations thereof.

19. A method for pest control in agriculture, horticulture and gardens, comprising covering the ground with the sheet of claim 1.

20. The sheet of claim 8 wherein said homopolymer or copolymer of a polyolefin is selected from the group consisting of low density polyethylene (LDPE), high density polyethylene (HDPE), polypropylene (PP), ethylene vinyl acetate (EVA), ethylene methyl acrylate (EMA), derivatives, mixtures and blends thereof.

21. The sheet of claim 1, wherein the optional pesticide is present in the herbicidal bottom layer and said optional pesticides is selected from the group consisting of at least one of an insecticide, at least one additional herbicide, and a mixture of at least two insecticides.

22. The sheet according to claim 15, wherein the organophosphorus insecticides are selected from the group consisting of chlorpyrifos and diazinon; the neonicotonoids are selected form the group consisting of imidacloprid, acetamiprid and thiamethoxam; the pyrethroid insecticides are selected from the group consisting of bifenthrin, lambda-cyhalothrin, tefluthrin, permathrin; the nematicides are selected from the group consisting of: cadusafos and fenamiphos; and spinosad, indoxacarb and fipronil.

23. The sheet according to claim 16, wherein the fungicides which are demethylation inhibitors are selected from the group consisting of hexaconazole, myclobutanil, propiconazole, triadimenol, tebuconazole, penconazole prochloraz, and metalaxyl.

24. The sheet according to claim 16, wherein the strobilurin type fungicides are selected from the group consisting of Azoxystrobin, Kresoxim-methyl, Trifloxystrobin, Metonimostrobin, Picoxystrobin, Pyraclostrobin and MA-20565.

* * * * *